United States Patent [19]
Okada et al.

[11] Patent Number: 5,952,489
[45] Date of Patent: Sep. 14, 1999

[54] TISSUE-SPECIFIC PROMOTER

[75] Inventors: Yukio Okada; Naohiro Yoshigi, both of Yaizu; Kazutoshi Ito; Makoto Kihara, both of Gunma-ken, all of Japan

[73] Assignee: Sapporo Breweries Limited, Tokyo, Japan

[21] Appl. No.: 08/793,599

[22] PCT Filed: Jul. 5, 1996

[86] PCT No.: PCT/JP96/01866

§ 371 Date: Mar. 4, 1997

§ 102(e) Date: Mar. 4, 1997

[87] PCT Pub. No.: WO97/02353

PCT Pub. Date: Jan. 23, 1997

[30] Foreign Application Priority Data

Jul. 5, 1995 [JP] Japan .................................. 7-191028

[51] Int. Cl.⁶ .............................. C12N 5/04; C12N 15/29; C12N 15/82; A01H 5/00
[52] U.S. Cl. ....................... 536/24.1; 536/23.6; 536/24.2; 435/320.1; 435/419; 435/468; 435/204; 800/278; 800/320; 800/287
[58] Field of Search .................................. 536/23.6, 24.2, 536/24.1; 435/172.3, 320.1, 419, 468, 204; 800/205, DIG. 9, DIG. 52, DIG. 55, 278, 320, 287

[56] References Cited

PUBLICATIONS

Wan and Lemaux. Plant Physiol. 1994. vol. 104: 37–48, 1994.
Matzke and Matzke. Plant Physiol. 1995. vol. 107:679–685, 1995.
Fernandez et al. Biochim Biophys Acta. 1993. vol. 1172 (3): 346–348, 1993.
Chen. Accession No. L10346. Feb. 5, 1993.
Jahn et al. Plant Cell Reports. 1991b. vol. 10: 1–6, 1991.
Lazzari et al. Theore. Appl. Genet. 1991. vol. 81: 437–444.

*Primary Examiner*—David T. Fox
*Assistant Examiner*—Ousama Zaghmout
*Attorney, Agent, or Firm*—Oblon, Spivak, McClelland, Maier & Neustadt, P.C.

[57] ABSTRACT

The invention provides a promoter capable of expressing an introduced gene in plant seeds, a vector comprising said promoter, a method for producing transgenic plants through transformation of plants with said vector, and a transgenic plant as transformed with said vector.

After a suitable foreign gene and a terminator are linked to the promoter, the resulting vector may be introduced into seeds of barley or other plants, thereby intentionally modifying the seeds and making the resulting seeds produce foreign substances therein.

27 Claims, 6 Drawing Sheets

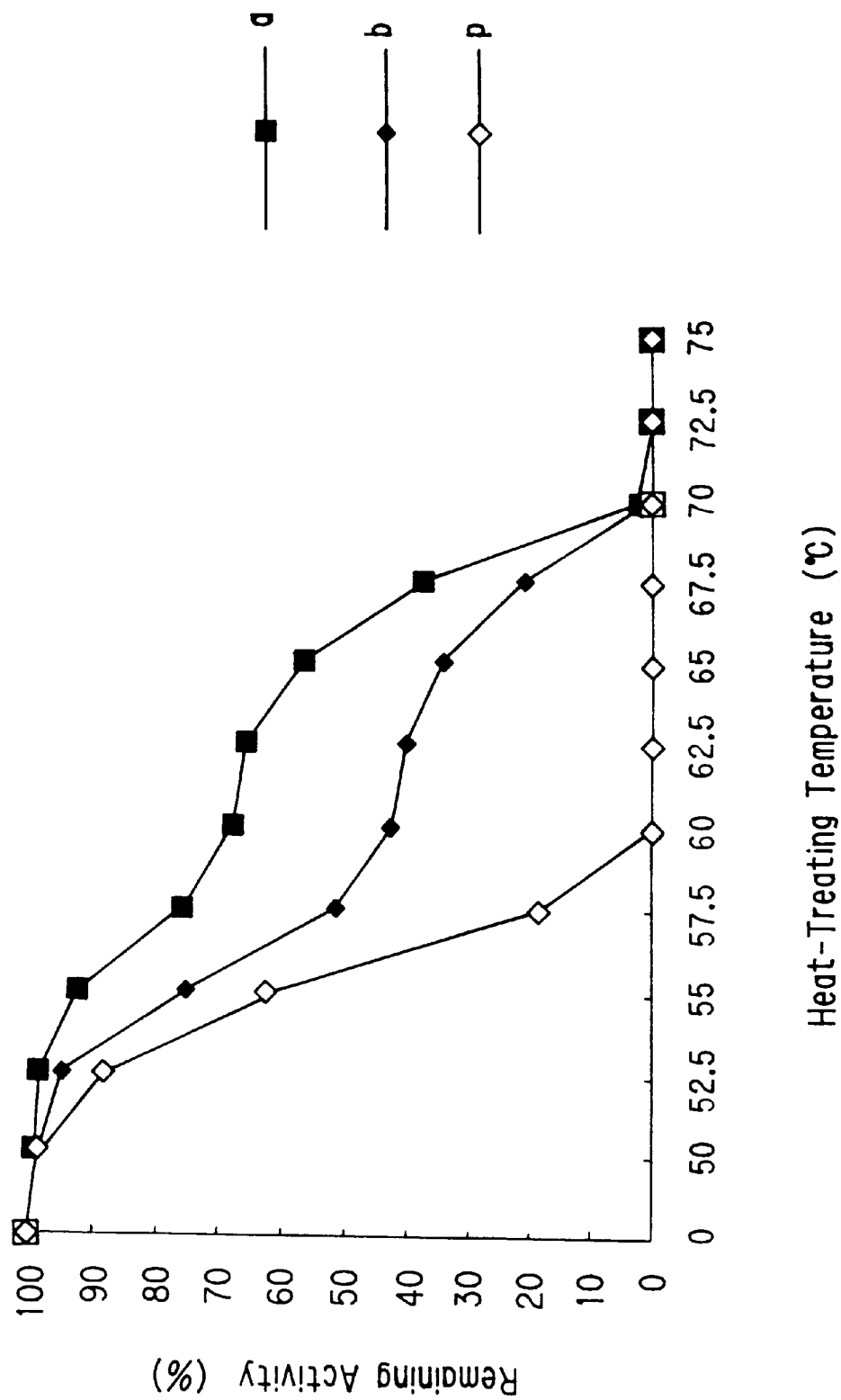

TISSUE-SPECIFIC PROMOTER

FIELD OF TECHNOLOGY

The present invention relates to a tissue-specific promoter, and particularly to a promoter for genes capable of being specifically expressed in plant seeds.

BACKGROUND TECHNOLOGY

Barley which is one example of plants is an essential agricultural crop for feed and for producing food and drink (beer, whisky, etc.), and is worldwide cultivated and consumed. In accordance with many uses for barley, various breeding in barley have heretofore been made. One conventional breeding in barley comprises selecting some effective varieties from artificial or natural mutants followed by combining them through mating or the like to thereby find out from a number of the resulting progeny the hybrids capable of expressing the intended phenotype. However, as comprising mating, the breeding of this type is problematic in that the genotype to be introduced is limited to one for relative mating and that it takes a long period of time to obtain the intended hybrids.

On the other hand, with the recent development in biotechnology such as genetic engineering technology and cell technology, a system for directly introducing a desirable gene into plants is being established even for barley, and is expected to be one capable of overcoming the problems in the conventional breeding (for example, BIOTECHNOLOGY 13, 248, 1995 is referred to for barley for brewing). The system requires a tissue-specific promoter. In this, precisely, where a foreign gene is introduced into a plant, the gene is required to be sufficiently expressed in the intended tissue in good time. For this purpose, a tissue-specific promoter must be linked to the foreign gene to thereby make the gene expressible under the control of the promoter.

The present invention is to provide a promoter capable of being specifically expressed in plant seeds. As one example, we, the inventors of the present invention have succeeded in the isolation of a promoter region that acts to control the transcription of a barley β-amylase gene and also in the analysis of the nucleotide sequence of the promoter region.

Barley β-amylase is a β-amylase obtainable from barley seeds (1,4-α-D-glucanmaltohydrolase [EC 3.2.1.2]), which is known as an enzyme usable, like soybean β-amylase, in the industrial production of maltose for injection and maltose for food and drink. It is also known that barley may be germinated to give malt which may be a raw material for beer and liquors. β-amylase existing in malt is one of the most important enzymes for the saccharification of starch in the step of mashing.

Regarding the gene of barley β-amylase, the complete sequence of cDNA of a variety of barley, Hiproly, which comprises 1754 bases, has been reported, and the amino acid sequence thereof comprising 535 residues has also been deduced (see Eur. J. Biochem., 169, 517, 1987).

In addition, the complete sequence of cDNA of a variety of barley, Haruna Nijo, which comprises 1775 bases, has been reported, and the amino acid sequence thereof comprising 535 residues has also been deduced (see J. Biochem., 115, 47, 1994; Japanese Patent Application Laid-Open No. 6-303983). Further, the complete sequence of the structural gene region of the chromosome DNA of the variety, Haruna Nijo, which comprises 3825 bases, has been reported (see Japanese Patent Application No. 7-92004).

However, regarding the promoter region that acts to control the transcription of such a β-amylase gene, there is no report referring to the isolation of the promoter gene, let alone the analysis of the nucleotide sequence thereof.

We, the present inventors, having attempted to isolate the promoter region of a barley β-amylase gene that may be actively expressed in barley developing seeds, thereby utilizing it in the improvement of barley seeds or in the production of products in barley seeds, have earnestly studied to attain this object, and, as a result, have completed the present invention.

According to the present invention, a desired foreign gene and a terminator therefor can be linked to the downstream site of the promoter region obtained, and introduced into plant such as barley, whereby the foreign gene can be expressed in the plant developing seeds. Thus, the promoter region can be utilized in the improvement of seeds of barley and other plants and also in the production of substances in such seeds.

SUMMARY OF THE INVENTION

The first aspect of the present invention is a promoter that acts to express an introduced gene in plant seeds.

The promoter includes, for example, one which has a molecular weight of 1.28 kb and which comprises cleavage sites to be cleaved with restriction enzymes, Sal I, Apa I, Xba I, Bam HI, Hind III, EcoT 221, Xba'I and Bam HI, in that order (this corresponds to the white area shown in FIG. 2), and one which comprises a gene substantially having the nucleotide sequence of Sequence Number 1 in Sequence Listing.

The second aspect of the present invention is a vector comprising said promoter.

The third aspect of the present invention is a method for producing transgenic plants, which comprises transformation of plants with said vector.

The fourth aspect of the present invention is a transgenic plant as transformed with said vector.

BRIEF DESCRIPTION OF THE DRAWINGS

FIG. 6 is a graph comparatively showing the thermophilicity of various β-amylases as extracted from the seeds of plant individuals derived from protoplasts into which was introduced a thermophilic β-amylase gene according to the present invention.

DETAILED DESCRIPTION OF THE INVENTION

Figure 1:
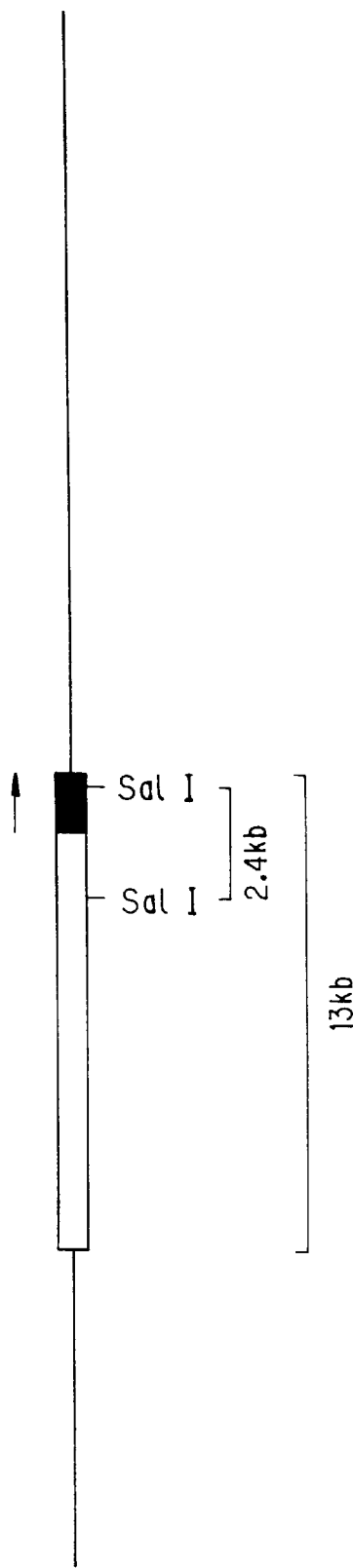
FIG. 1 is a physical map showing a clone that comprises the promoter region of a β-amylase gene.

As has been mentioned hereinabove, barley β-amylase is a β-amylase (1,4-α-D-glucanmaltohydrolase [EC 3.2.1.2]) to be obtained from barley seeds.

Of the gene of this enzyme, the complete sequence of cDNA as derived from particular varieties of barley has been reported, as has been mentioned hereinabove. However, regarding the promoter region that acts to control the transcription of such a β-amylase gene, there is as yet no report referring to the isolation of the promoter gene and to the analysis of the nucleotide sequence thereof.

It is known that, in barley plants, barley β-amylase is specifically produced in the developing seeds, and that the enzyme is an essential protein that accounts for approximately from 1 to 2% of the soluble proteins in the endosperm (see Hereditas, 93, 311, 1980).

Having known the above, we, the present inventors expected that a promoter region capable of being specifically expressed in plant seeds could be utilized as the transcriptional control factor for a foreign gene to be introduced into plant for the purpose of making the plant seeds produce the foreign gene-related substance. In addition, for barley, we specifically noted that the isolation as well as the identification of the promoter region of a barley β-amylase gene is important in order to successfully introduce a foreign gene into barley by the use of the promoter.

To concretely illustrate the present invention, one process is described in detail hereinunder which comprises isolating and analyzing the promoter region of a barley β-amylase gene, constructing an expression vector that comprises the promoter region, introducing the expression vector into plant along with a foreign gene, and making the thus-transformed seeds express the foreign gene.

The "gene substantially having the nucleotide sequence of Sequence Number 1 in Sequence Listing" as referred to herein means that the gene allows any deletion, substitution and addition of some bases in said sequence so far as the gene has the significant promoter activity in plant seeds.

(1) Preparation of Barley Chromosome DNA:

In barley, the same barley chromosome DNA exists in all cells of every tissue. From barley seeds as germinated in vermiculite in the dark at 20° C. for 7 days, the primary leaves can be processed herein to give the intended barley chromosome DNA. The preparation of the DNA can be conducted by any known method. For example, referred to is the method described in "Cloning and Sequencing—Manuals for Experiments in Plant Biotechnology" (published by Nohson Bunka Publishing Co., 1989), page 252.

(2) Formation of Barley Genomic Library:

Using the barley chromosome DNA, a barley genomic library can be formed by any known method. For example, referred to is the method described in "Cloning and Sequencing—Manuals for Experiments in Plant Biotechnology" (published by Nohson Bunka Publishing Co., 1989), page 272.

(3) Formation of Probe:

Probes to be used for screening the barley genomic library can be formed by labeling a suitable DNA fragment, or that is, a DNA fragment having a sequence that is complementary to the sequence of the gene to be selected through the screening, with DIG-High Prime (produced by Boehringer Mannheim Co.).

(4) Cloning of Promoter Region of Barley β-amylase Gene:

To clone the promoter region of the barley β-amylase, the barley genomic library may be screened by the use of the probe as formed in the above (3). This screening can be effected by any known method. For example, referred to is the method described in "Cloning and Sequencing—Manuals for Experiments in Plant Biotechnology" (published by Nohson Bunka Publishing Co., 1989), page 134. The detection of the intended clones can be effected by the use of DIG Luminescent Detection Kit (produced by Boehringer Mannheim Co.).

(5) Sequencing:

The promoter region can be sequenced, for example, according to the Maxam-Gilbert chemical degradation of DNA method (see Methods in Enzymology, 65, 499, 1980) or the Sanger dideoxy-mediated chain-termination method (see Gene, 19, 269, 1982).

(6) Constrution of Reporter Plasmid:

To determine the promoter activity of the promoter region thus obtained through the steps mentioned above, a reporter gene, such as a β-gluclonidase gene (GUS), and a terminator, such as a nopalin synthetase gene (NOS) terminator, may be linked to the downstream site of the promoter region to form a reporter plasmid, and the activity of the product translated from the reporter gene may be measured. As the reporter gene and the terminator, usable are commercially-available products, such as plasmid pBI 101 (produced by Clontech Co.).

(7) Detection of Promoter Activity in Endosperm Cells of Developing Seeds:

To determine the promoter activity in endosperm cells of developing seeds by the use of the reporter plasmid as constructed in the above, any known method can be employed (see Plant Cell Reports, 10, 595, 1992). Briefly, a protoplast is prepared from endosperm cells of developing seeds, into which is introduced the reporter plasmid according to a known method, for example, a polyethylene glycol method (see, for example, Theor. Appl. Genet., 91, 707, 1995; Japanese Patent Application Laid-Open No. 7-184492), and the GUS activity in the resulting cell lines is measured.

(8) Formation of Transgenic Plant:

Using the promoter of a barley β-amylase gene of the present invention, an expression vector is constructed. Then, the vector is introduced into plant cells to obtain a transgenic plant.

As one example, the expression vector plasmid for use in the present invention comprises a thermophilic β-amylase gene as the gene to be expressed, the promoter of the invention as the transcriptional control factor, and a cauliflower mosaic virus 35S terminator as the terminator. This expression vector plasmid is introduced into plant, which thereby can produce the intended thermophilic β-amylase in seeds.

The thermophilic β-amylase gene to be linked to the promoter may be any organism-derived one or may even be any modified one to be prepared by modifying the organism-derived gene. We, the present inventors employed herein a thermophilic β-amylase gene as obtained through site-specific mutation of a barley β-amylase gene (see Japanese Patent Application Laid-Open No. 7-327681).

In order to directly introduce the recombinant plasmid into plant cells, employable is any of electroporation methods (for example, see Nature, 319, 791, 1986), polyethylene glycol methods, particle gun methods (for example, see Nature, 327, 70, 1987), laser perforation methods (for example, see Barley Genetics VI, 231, 1991), Agrobacterium methods (for example, see Plant J., 6, 271, 1994) and others. We, the present inventors employed herein barley as the test material and a polyethylene glycol method using protoplasts as the gene introduction method.

Barley protoplasts can be prepared preferably from an immature embryo-derived callus (see Kihara & Funatsuki, 1995, Plant Sci., 106: 115–120; Japanese Patent Application Laid-Open No. 7-213183) or from suspension culture cells with regeneration ability as established from such an immature embryo-derived callus (see Kihara & Funatsuki, 1994, Breeding Sci., 44: 157–160; Funatsuki & Kihara, 1994, Plant Cell Rep., 13: 551–555; Japanese Patent Application Laid-Open No. 4-360633), according to any ordinary protoplast preparation method using cellulase and pectinase.

After the formation of colonies from the protoplasts, the liquid medium and the cell suspension used as nurse cells are removed, and the colonies are further cultured in a liquid medium containing a selective reagent, such as geneticin (G418), hygromycin, bialafos or the like. Thus, only resistant colonies grow in the medium.

The thus-grown colonies are transferred onto a solid medium containing any of the selective reagents, geneticin (G418), hygromycin, bialafos and others. Further culture on the solid medium gives embryogenic calluses or embryoids, which are then transferred onto a different solid medium containing no selective reagent, resulting in their regeneration into plant.

The thus-grown plant individuals are then transplanted in pots and are cultivated therein under ordinary cultivation conditions, for example, at a daylength of 16 hours, at 10,000 luxes and at 18° C., thereby being fertile transgenic plants.

From the seeds obtained from the plants, extracted is β-amylase, which is then heat-treated. The activity of the thus heat-treated enzyme is measured to determine its thermophilicity. The amylase activity can be measured through saccharification of starch with the enzyme. We, the present inventors employed herein an amylase determination reagent (Diacolor AMY, trade name of a product of Ono Pharmaceutical Co.), with which only the activity of β-amylase can be selectively determined even in a small amount of a sample containing the enzyme.

EXAMPLES

Now, the present invention will be described in detail hereinunder with reference to the following examples, which, however, are not intended to restrict the scope of the present invention.

Example 1
Preparation of Barley Chromosome DNA:

About 1000 grains of barley (Haruna Nijo) were germinated in vermiculite in the dark at 20° C. for 7 days. The primary leaves (about 65 g) thus grown were taken off and then cut into fine pieces of about 1 cm long, from which was prepared a chromosome DNA. As a result, about 1 mg of DNA was extracted from 10 g of the leaves.

Example 2
Formation of Barley Genomic Library:

150 μg of the chromosome DNA as prepared in Example 1 was partially digested with 1 U of Sau 3AI, at 37° C. for 1 hour, and the resulting fragments were fractionated according to sucrose density gradient centrifugation. The fraction comprising fragments of about 18 kb was purified and inserted into a λ phage vector EMBL3 (produced by Stratagene Co.). Using Gigapack II Gold (produced by Stratagene Co.), the resulting vector was packaged into lambda phage particles, with which *Escherichia coli* XL1-Blue MRA(P2) (produced by Stratagene Co.) were transformed.

Example 3
Formation of Probe:

A barley β-amylase structural gene-derived Eco RV-Hind III fragment described in Japanese Patent Application No. 7-92004, or that is, the DNA fragment having the nucleotide sequence of Sequence Number 2 in Sequence Listing was labeled with digoxigenin, using DIG-High Prime (produced by Boehringer Mannheim Co.), to obtain a probe.

Example 4
Cloning of Promoter Region of Barley β-amylase Gene:

The plaque of the barley genomic library as formed in Example 2 was transferred onto a nylon membrane, "Hybond N" (produced by Amersham Co.), and then screened through ordinary plaque hybridization using the probe as formed in Example 3. To detect the intended clone, used was DIG Luminescent Detection Kit (produced by Boehringer Mannheim Co.). As a result, one positive clone was obtained. This clone had the 5'-terminal region of the β-amylase structural gene and the upstream region containing a promoter region for the gene.

The physical map of the thus-obtained clone is shown in FIG. 1, in which the abbreviations indicate the sites that are recognized and cleaved by the indicated restriction enzyme, the thin lines indicates the vector sites, the black area indicates the 5'-terminal region of the β-amylase structural gene, and the white area indicates the upstream site containing the promoter region. The arrow therein indicates the direction of the β-amylase gene.

Example 5
Sequencing of Promoter Region of β-amylase Gene:

From the positive clone as obtained in Example 4, cleaved out was the Sal I-Sal I fragment of 2.4 kb composed of the 5'-terminal region of the β-amylase structural gene and the promoter region. This fragment was inserted into a plasmid pUC119, from which was formed a deletion clone using Kilo-Sequence Deletion Kit (produced by Takara Shuzo Co.). After this, the promoter region was sequenced according to Sanger dideoxy-mediated chain-termination method.

Figure 2:
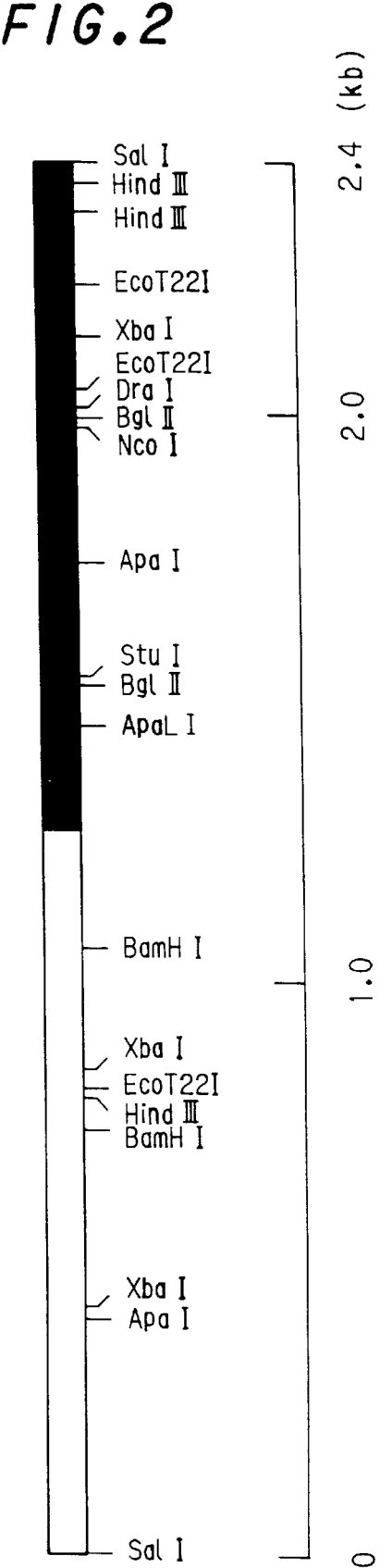
FIG. 2 is a physical map showing a 2.4 kb Sal I-Sal I fragment that comprises the 5'-terminal region of a structural gene of a β-amylase gene and the promoter region of the β-amylase gene.

The physical map of the 2.4 kb Sal I-Sal I fragment is shown in FIG. 2, in which the abbreviations indicate the sites that are recognized and cleaved by the indicated restriction enzymes, the black area indicates the 5'-terminal region of the β-amylase structural gene, and the white area indicates the upstream site containing the promoter region.

The nucleotide sequence of the thus-sequenced promoter region of the β-amylase gene is Sequence Number 1 in Sequence Listing. The partial nucleotide sequence of the 2.4 kb Sal I-Sal I fragment thus sequenced is Sequence Number 3 in Sequence Listing. Comparing the nucleotide sequence of the 5'-terminal region of the β-amylase structural gene with the barley β-amylase structural gene that had already been obtained (see Japanese Patent Application No. 7-92004), it was confirmed that the DNA fragment obtained herein is a β-amylase gene. The promoter region sequenced herein contained a TATA box which widely exists in promoter regions in eucaryotes.

Figure 3:
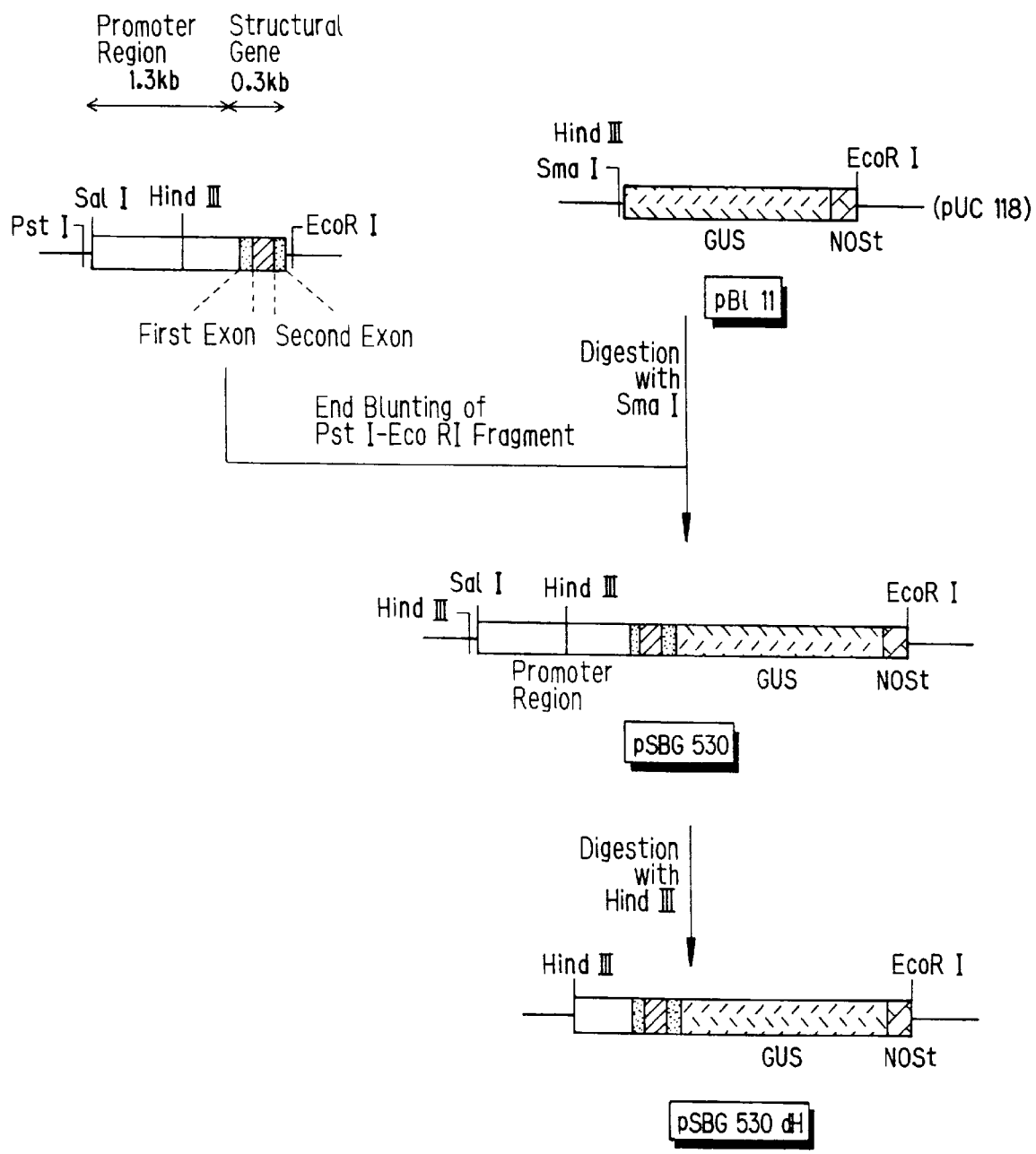
FIG. 3 shows a process for constructing a reporter plasmid.

Example 6
Formation of Reporter Plasmid:

A reporter plasmid was formed in accordance with the method illustrated in FIG. 3. Precisely, a Hind III-Eco RI fragment comprising the GUS gene and the NOS terminator of a plasmid pBI 101 (produced by Clontech Co.) was inserted into the Hind III-Eco RI site of a plasmid pUC 118 to prepare a plasmid pBI 11.

On the other hand, of the fragment of Sequence Number 3 which is comprised of from the 1st to the 1672nd bases of the nucleotide sequence of the deletion clone as formed in Example 5, or that is, the plasmid composed of the promoter region of Sequence Number 1 and the 341 bp 5'-terminal region of the β-amylase structural gene, cleaved out was a Pst I-Eco RI fragment containing said promoter region. The ends of the thus-cleaved Pst I-Eco RI fragment were blunted, using a blunting kit (produced by Takara Shuzo Co.), and the thus-blunted fragment was inserted into the Sma I site of the plasmid pBI111 to give a reporter plasmid pSBG 530.

Further, the Hind III-Hind III fragment that codes for the 5'-terminal side of the β-amylase promoter region of the plasmid pSBG 530 was removed from the plasmid to give another reporter plasmid pSBG 530 dH.

Example 7
Detection of Promoter Activity in Endosperm Cells in Developing Seeds:

The activity of the isolated promoter region of the β-amylase gene in endosperm cells in developing seeds was determined in a transient assay system using the reporter plasmids formed in Example 6.

First, developing seeds of a variety of barley, Bomi that had been harvested in about 14 days from the blooming were peeled to remove their husks, then sterilized once with 70% ethanol and once again with a ⅕ dilution of hypochlorous acid, and thereafter washed water for a total of three times. The endosperm was extracted out from these, and processed overnight with a CPW solution (0.2 mM $KH_2PO_4$, 10 mM $CaCl_2$, 1 mM $MgSO_4$, 1 mM $KNO_3$) containing 0.4% cellulase and 11% mannitol, at 25° C.

The resulting protoplasts were washed with the CPW solution containing 11% mannitol, and then divided into plural sections of $10^6$ protoplasts each per one transformation system. To each protoplast section, added were 30 μg of the DNA and 200 μl of a C100S solution (7% sorbitol, 10 mM $CaCl_2$, 4.7 mM MES, pH 5.7) and suspended. The resulting suspension was then processed with 0.5 ml of the C100S solution (pH 7.0) containing 40% polyethylene glycol 1540 added thereto, for 10 minutes.

To this was added 10 ml of an LW solution (see Lazzeri et al., Theor. Appl. Genet., 81:437, 1991), and the resulting mixture was centrifuged. 3 ml of an L1 medium (see Theor. Appl. Genet., 81:437, 1991) was added to the resulting residue, which was then incubated overnight at 25° C. 20 ml of the LW solution was added to the resulting culture, which was then centrifuged. The resulting residue was suspended in 200 μl of a GUS extract (0.05 M $NaPO_4$, 0.01 M EDTA, 0.1% sarcosine, 0.1% Triton X-100, 0.1% 2-mercaptoethanol), and the suspension was then frozen and thawed repeatedly twice. This was centrifuged, and the resulting supernatant was used as a crude enzyme solution for the determination of the promoter activity.

Precisely, the crude enzyme solution obtained hereinabove was reacted with 4-methylumbelliferyl-β-D-gluclonide, then the reaction was stopped with 0.2 M sodium carbonate solution, and the 4-methylumbelliferyl residue produced was quantified, from which was determined the promoter activity. To quantify the protein, used was "Protein Assay" produced by Bio-Rad Co.

Figure 4:
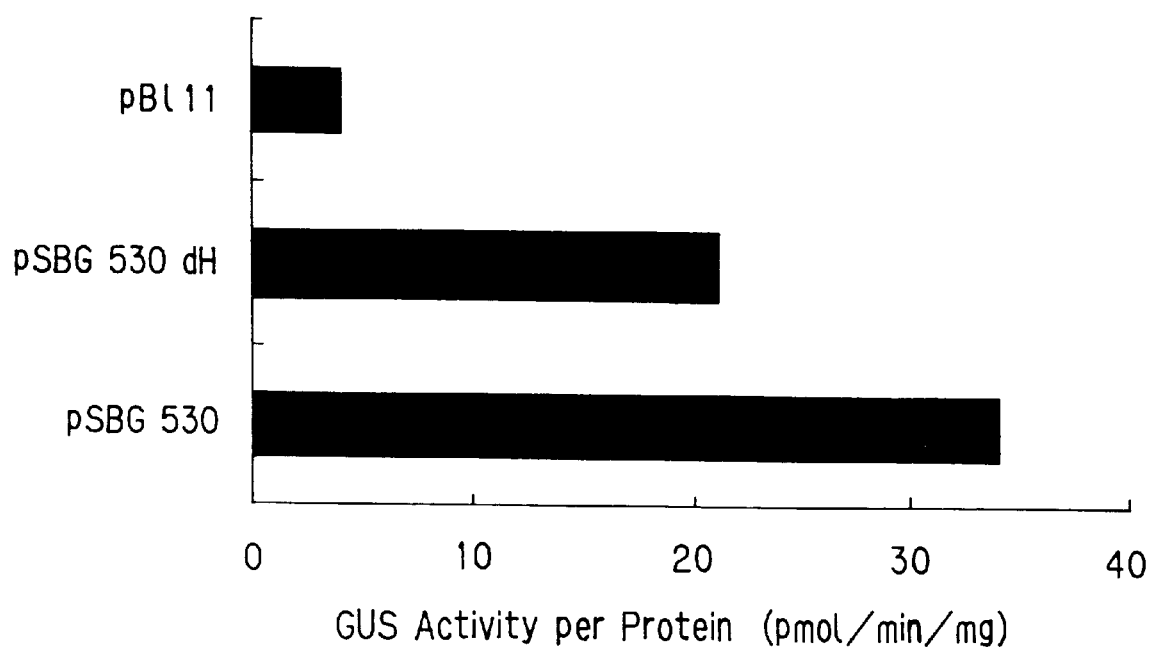
FIG. 4 is a graph showing the GUS activity of various cell lines.

The GUS activity in each cell line is shown in FIG. 4, from which it is confirmed that the isolated β-amylase promoter region was active in the endosperm cells of developing barley seeds. The GUS activity in the cell line introduced pSBG 530dH was lowered to about ⅔ of that in the cell line introduced pSBG 530, from which it is confirmed that the promoter region requires the nucleotide sequence of Sequence Number 1 in Sequence Listing.

Example 8
Formation of Transgenic Plant:

In accordance with the method of Kihara & Funatsuki (1994, Breeding Sci., 44:157–160) or the method of Funatsuki & Kihara (1994, Plant Cell Rep., 13:551–555), immature embryos having a length of approximately from 0.5 to 1.0 mm of a variety of barley, Igri, were placed onto L2 medium for callus indication. After one month, the thus-formed calluses were transferred onto an L1 liquid medium and cultured therein for from 2 to 4 months by shaking culture, while being exposed to weak light (at 500 luxes). Thus was formed a liquid suspension culture comprising cell masses having a diameter of approximately from 1 to 3 mm.

To 1 g of the cells, added were about 10 ml of an enzyme solution (1.0% Cellulase Onozuka RS, 0.1% Pectolyase Y-23, 5 mM MES dissolved in LW solution) and the resulting mixture was left statically at 25° C. for 2 to 3 hours.

The thus-obtained protoplast suspension was filtered through a 64-μ mesh membrane and a 26-μ mesh membrane, and then centrifuged to collect the protoplasts. Then, these were washed with an LW solution for a total of three times.

Figure 5:
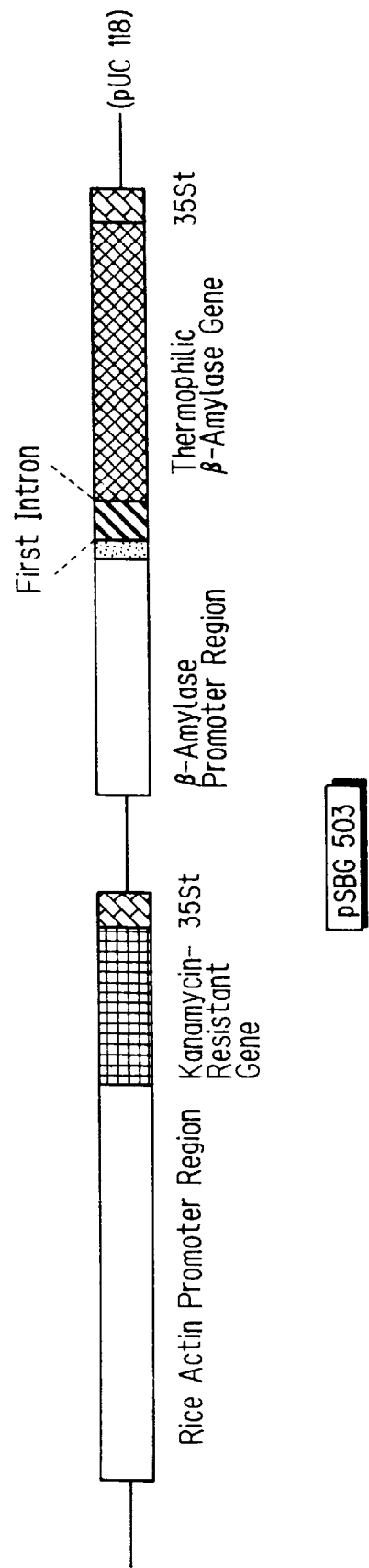
FIG. 5 shows an expression vector pSBG503 of a thermophilic β-amylase.

Next, from $1 \times 10^6$ to $3 \times 10^6$ protoplasts thus obtained were suspended in 250 μl of a liquid medium, Ca-S which comprised 10 μg/ml of a plasmid pSBG503 (expression vector for thermophilic β-amylase-see FIG. 5), 100 mM of $CaCl_2$, 0.6 M of sorbitol and 0.1% of MES and which had been adjusted to pH 5.7. The plasmid pSBG503 comprised a kanamycin-resistant gene and a thermophilic β-amylase gene, in which a rice actin promoter and a cauliflower mosaic virus 35S terminator (35St) were linked to the kanamycin-resistant gene while the barley β-amylase promoter region of Sequence Number 1 and a cauliflower mosaic virus 35S terminator were to the thermophilic β-amylase gene, each as the transcriptional control factor and the terminator, respectively. The thermophilic β-amylase gene comprised the first intron of a barley β-amylase gene. To the resulting suspension was dropwise added 600 μl of Ca-S which contained 40% of polyethylene glycol and which had been adjusted to pH 7.0. This was statically left as it was for 10 minutes, while being shaken at intervals of 5 minutes. This was diluted with 10 ml of an LW solution and then centrifuged to collect the protoplasts.

The thus-collected protoplasts were then suspended in 1 ml L1 medium containing 0.6 M maltose, 2.0 mg/liter 2,4-D and 1.8% agarose, and immediately spread over a 6-cm Petri dish to make thereon a disc having a diameter of about 4.5 cm. After having been solidified, the resulting solid was peeled off from the dish, and then incubated in 5 ml of a liquid medium (this comprised of the same components as those constituting the medium used hereinabove to make the protoplast suspension) which contained 200 mg/ml of barley suspension cells, with shaking at a shaking speed of 50 rpm.

On 15 days after the start of the culture of the protoplasts, the liquid medium and the suspension cells were removed, and 3 ml of a liquid medium containing 20 μg/ml of Geneticin (G418) was added to the protoplast culture. Then, the resulting protoplast culture was further cultured for 14 days with shaking, resulting in the growth of resistant colonies in agarose and therearound and also in the liquid medium.

The thus-grown colonies were transferred onto L3 medium containing 20 μg/ml Geneticin (G418) and containing, as hormones, 0.5 mg/liter of 2,4-D and 1.0 mg/liter benzylaminopurine (BAP). On 3 to 15 days after the transfer, embryogenic calluses or embryoids were found to grow on the selection medium.

These calluses or embryoids were transferred onto L3 medium not containing any selective reagent but containing 0.5 mg/liter 2,4-D and 1.0 mg/liter BAP. To this stage, the incubation was conducted under weak lighting (at about 500 luxes) at 25° C. After about 3 to 15 days, regeneration of shoots was observed from the calluses or embryoids. After having been sufficiently shoot development, these were transferred into a light place where they were exposed to strong light of about 7000 luxes.

The thus-grown barley plantlets were then transplanted onto L3 medium not containing any hormone, for the induction of root development. After about one month, these were transplanted in pots. After having been thus transplanted in pots, these were cultivated therein at a daylength of 16 hours, at 10,000 luxes and at 15° C., thereby being a large number of transgenic barley plants. The presence or absence of the thermophilic β-amylase gene fragment in the thus-grown barley plants was checked through polymerase chain reaction (PCR), which verified the presence of the fragment therein.

From the developing seeds these barley plants, extracted was an amylase using 50 mM acetate buffer containing 10 mM DTT. The thus-extracted enzyme was heat-treated at temperatures falling between 50 and 75° C. (varying at intervals of 2.5° C.) for 30 minutes, and the β-amylase activity of the enzyme was measured, using Diacolor AMY, to determine its thermophilicity. The results are shown in FIG. 6.

As is obvious from the data in FIG. 6, it was verified that the seed samples, a and b, both having the thermophilic β-amylase gene as introduced thereinto contained the intended thermophilic β-amylase as accumulated therein, while the control seed sample, p, derived from the protoplasts not having the thermophilic β-amylase gene did not contain it. In particular, it is known that the accumulation of the thermophilic β-amylase in the seed sample, a, is remarkable.

Possibility of Industrial Utilization

According to the present invention, there is provided a promoter for a gene capable of being specifically expressed in plant seeds. In particular, the present invention has clarified the nucleotide sequence of the promoter region for a β-amylase gene and has clarified the activity of the promoter in developing seeds. After a suitable foreign gene and a terminator are linked to the promoter, the resulting vector may be introduced into seeds of barley or other plants, thereby intentionally modifying the seeds of barley or other plants. In addition, it is also possible to make the resulting transgenic plant seeds produce foreign substances therein. Thus, the present invention produces many advantages in the field of plant breeding.

We claim:

1. An isolated barley β-amylase promoter comprising SEQ ID NO: 1.

2. The promoter of claim 1, which has a molecular weight of 1.28 kb and comprises the following restriction sites in the order: Sal I, Apa I, Xba I, Bam HI, Hind III, EcoT 221, Xba I and Bam HI.

3. The promoter of claim 1, which comprises the nucleic acid sequence of SEQ ID NO: 1.

4. A nucleic acid comprising the promoter of claim 1 operably linked to a heterologous gene.

5. The nucleic acid of claim 4, wherein the heterologous gene is a thermophilic β-amylase gene.

6. A vector comprising the nucleic acid of claim 4.

7. A vector comprising the nucleic acid of claim 5.

8. A plant cell transformed with the vector of claim 7.

9. The transformed plant cell of claim 8, which is a barley plant cell.

10. The transformed plant cell of claim 9, which is a an endosperm cell.

11. A plant cell transformed with the vector of claim 7.

12. The transformed plant cell of claim 11, which is a barley plant cell.

13. The transformed plant cell of claim 12, which is a an endosperm cell.

14. A method of making a transformed plant cell, comprising transforming a plant cell with the vector of claim 6.

15. The method of claim 14, wherein the plant cell is a barley plant cell.

16. The method of claim 15, wherein the barley plant cell is a an endosperm cell.

17. A method of making a transformed plant cell, comprising transforming a plant cell with the vector of claim 7.

18. The method of claim 17, wherein the plant cell is a barley plant cell.

19. The method of claim 18, wherein the barley plant cell is a an endosperm cell.

20. A plant transformed with the vector of claim 6.

21. The transformed plant of claim 20, which is a barley plant.

22. A plant transformed with the vector of claim 7.

23. The transformed plant of claim 22, which is a barley plant.

24. A method of malking a transformed plant, comprising transforming a plant with the vector of claim 6.

25. The method of claim 24, wherein the plant is a barley plant.

26. A method of making a transformed plant, comprising transforming a plant with the vector of claim 7.

27. The method of claim 26, wherein the plant is a barley plant.

* * * * *

SEQUENCE LISTING

<160> NUMBER OF SEQ ID NOS: 3

<210> SEQ ID NO 1
<211> LENGTH: 1276
<212> TYPE: DNA
<213> ORGANISM: Barley

<400> SEQUENCE: 1

```
gtcgacacat catcttgaga acgtcttctc taactgaatg ccaattgctg aaaggcatga        60
aataaattaa ggaaacttgc aaacacaaat gtcaagtctg agacttgaac tctagtggac       120
acgtttgaac attaatgtgc ggttttggtg aaagtgaaaa aacagttgac atccttgtga       180
atgaatcaat tcaaaccaaa tgcaaaaatg agaagtgaaa accccataat cgtcgtttgt       240
agaaaacaaa taacactgaa actaatgggg taatttctga gaaactataa ttggtgaggc       300
acattctcat ttgattgttt agtttaactt ccttctcaca ttatttttc ctagagtatc        360 tcattgctcg ggtggcatcc aaattttcca gacaagggcc catgcaatgg ttctagatga       420
ttggaaaaca aatattaaat attttttgtag atgattgtat tagtgtcgca aacatgcaac       480
acaattttcg tcggaaaaaa aaacaaattt aggatgacat tttggggtaa cttttggtgt       540
tcaatttgtt tttttggcac aagccaaaat gtttaaccctt tttacctcaa aattgcagg       600 tagcatttag atatgactaa gtatataaat aaattttgtc ttgatttttt ttcatttga         660 atttttttgg cccccgaagc atattcttcc gggagccaaa ttgacattcc ggtcatgatg       720
tggcttggat cccaagttag tcatacagat aaggatatat cttacctcaa ccgaatctag       780
gttacaacaa gcttaacact catgcattag tgtccatcct agactcctct agaaggcaat       840
ggtttacaca ccattgtggt ttgtacaaat tccaacactc ttcctcaatc ataactttat       900
```

-continued

```
gaagtcgaga ttgatcttaa agttctgatg ttatctgtta aagaatagct tgggaaacac      960
atgtacaact taagtcagga tgtgtgcgtc ttcacttcgt atagggtgcc gtttggttga     1020
gagttgagac gtggattgga tcccacgtta gctataatat agataatgat cccatctctc     1080
tcccaatcag acctcaatcc ttgaagtttg gctgtgtgtg gtaaagaaaa ccaaaattag     1140
ttcacaaagc gcccttctg agtggacaat cctatttctg acatatctga ttggaaagct      1200
aggttcgccg ttggcctcac atctatggat acatcttttt catagtataa atagacccttt    1260 ttattaagct ccctgc                                                     1276
```

<210> SEQ ID NO 2
<211> LENGTH: 1066
<212> TYPE: DNA
<213> ORGANISM: Barley

<400> SEQUENCE: 2

```
gatatccaac aaaccatttg aagttgtaga gcatcatcca tagccagcat ccacaatgga       60
ggtgaacgtg aaaggcaact atgtccaagt ctacgtcatg ctccctgtaa gctccatcca      120
ttcagaccaa tcgctgagaa ccacacacta aaactatttc aaggatctag tgcacacata      180
tacattattg ttgtacatat aacattgata cttcttgtaa aactctaatt caaagggtga      240
agaacaagat ctgaggcctc aaatgagtat tttatttgta ctaaccttga ctacacttcc      300
attgttgaaa taaataaata gctggacgcc gtgagcgtga acaacaggtt cgagaagggc      360
gacgagctga gggcgcaatt gaggaagctg gtagaggccg gtgtggatgg tgtcatggta      420
gacgtctggt ggggcttggt ggagggcaag ggccccaagg cgtatgactg gtccgcctac      480
aagcagttgt ttgagctggt gcagaaggct gggctgaagc tacaggccat catgtcgttc      540
caccagtgtg gtggcaacgt cggcgacgcc gtcaacatcc caatcccaca gtgggtgcgg      600
gacgtcggca cgcgtgatcc cgacattttc tacaccgacg gtcacgggac taggaacatt      660
gagtacctca ctcttggagt tgataaccag cctctcttcc atggaagatc tgccgtccag      720
gttactttaa accaccactc tagttctctg atgcatattt atatagaagt tcaagatgac      780
accaaataca agcaaaaggt taaggtgcc aaaaacagat aagcaaagaa acaaaaccta       840
gctaatgaaa cagtctagag cctatcaaaa aaaaaaaaaa aacatcgaga aggtgcctag      900
agcggatggg tttcgacaac cctttagctt tcatgcatct ttttgggaaa gggtgaaaaa      960
caccgtcctt taagtcgatt gatgcaggca gccttctatt gtttgtaagc tatcaggaaa     1020
tacaaaatta atagctagtt gtcattttaa tagttgtagc aagctt                    1066
```

<210> SEQ ID NO 3
<211> LENGTH: 2142
<212> TYPE: DNA
<213> ORGANISM: Barley

<400> SEQUENCE: 3

```
gtcgacacat catcttgaga acgtcttctc taactgaatg ccaattgctg aaaggcatga       60
aataaattaa ggaaacttgc aaacacaaat gtcaagtctg agacttgaac tctagtggac      120
acgtttgaac attaatgtgc ggttttggtg aaagtgaaaa aacagttgac atccttgtga      180
atgaatcaat tcaaaccaaa tgcaaaaatg agaagtgaaa accccataat cgtcgtttgt      240
agaaaacaaa taacactgaa actaatgggg taatttctga gaaactataa ttggtgaggc      300
acattctcat ttgattgttt agtttaactt ccttctcaca ttattttttc ctagagtatc      360
tcattgctcg ggtggcatcc aaattttcca gacaagggcc catgcaatgg ttctagatga      420
```

-continued

```
ttggaaaaca aatattaaat atttttgtag atgattgtat tagtgtcgca aacatgcaac      480
acaattttcg tcggaaaaaa aaacaaattt aggatgacat tttggggtaa cttttggtgt      540
tcaatttgtt tttttggcac aagccaaaat gtttaacctt tttacctcaa aatttgcagg      600
tagcatttag atatgactaa gtatataaat aaattttgtc ttgattttttt ttcattttga     660 attttttttgg cccccgaagc atattcttcc gggagccaaa ttgacattcc ggtcatgatg    720
tggcttggat cccaagttag tcatacagat aaggatatat cttacctcaa ccgaatctag     780
gttacaacaa gcttaacact catgcattag tgtccatcct agactcctct agaaggcaat     840
ggtttacaca ccattgtggt ttgtacaaat tccaacactc ttcctcaatc ataactttat     900
gaagtcgaga ttgatcttaa agttctgatg ttatctgtta aagaatagct tgggaaacac     960
atgtacaact taagtcagga tgtgtgcgtc ttcacttcgt ataggtgcc gtttggttga     1020 gagttgagac gtggattgga tcccacgtta gctataatat agataatgat cccatctctc    1080
tcccaatcag acctcaatcc ttgaagtttg gctgtgtgtg gtaaagaaaa ccaaaattag    1140
ttcacaaagc gcccttttctg agtggacaat cctatttctg acatatctga ttggaaagct   1200
aggttcgccg ttggcctcac atctatggat acatcttttt catagtataa atagaccctt   1260
ttattaagct ccctgccata tccaacaaac catttgaagt tgtagagcat catccatagc   1320
cagcatccac aatggaggtg aacgtgaaag gcaactatgt ccaagtctac gtcatgctcc   1380
ctgtaagctc catccattca gaccaatcgc tgagaaccac acactaaaac tatttcaagg   1440
atctagtgca cacatataca ttattgttgt acatataaca ttgatacttc ttgtaaaact   1500
ctaattcaaa gggtgaagaa caagatctga ggcctcaaat gagtatttta tttgtactaa   1560
ccttgactac acttccattg ttgaaataaa taaatagctg gacgccgtga gcgtgaacaa   1620
caggttcgag aagggcgacg agctgagggc gcaattgagg aagctggtag aggccggtgt   1680
ggatggtgtc atggtagacg tctggtgggg cttggtggag ggcaagggcc ccaaggcgta   1740
tgactggtcc gcctacaagc agttgtttga gctggtgcag aaggctgggc tgaagctaca   1800
ggccatcatg tcgttccacc agtgtggtgg caacgtcggc gacgccgtca acatcccaat   1860
cccacagtgg gtgcgggacg tcggcacgcg tgatcccgac attttctaca ccgacggtca   1920
cgggactagg aacattgagt acctcactct tggagttgat aaccagcctc tcttccatgg   1980
aagatctgcc gtccaggtta ctttaaacca ccactctagt tctctgatgc atatttatat   2040
agaagttcaa gatgacacca aatacaagca aaaggttaaa ggtgccaaaa acagataagc   2100
aaagaaacaa aacctagcta atgaaacagt ctagagccta tc                       2142
```